United States Patent
Vadasz et al.

(10) Patent No.: US 10,736,939 B2
(45) Date of Patent: Aug. 11, 2020

(54) SEMAPHORIN 3A FOR TREATMENT AND ASSESSMENT OF SEVERITY OF INFLAMMATORY BOWEL DISEASE

(71) Applicant: Medical Research & Development Fund for Health Services Bnai Zion Medical Center, Haifa (IL)

(72) Inventors: Zahava Vadasz, Haifa (IL); Elias Toubi, Haifa (IL)

(73) Assignee: Medical Research & Development Fund for Health Services Bnai Zion Medical Center, Haifa (IL)

( * ) Notice: Subject to any disclaimer, the term of this patent is extended or adjusted under 35 U.S.C. 154(b) by 0 days.

(21) Appl. No.: 15/549,469

(22) PCT Filed: Feb. 9, 2016

(86) PCT No.: PCT/IL2016/050146
§ 371 (c)(1),
(2) Date: Aug. 8, 2017

(87) PCT Pub. No.: WO2016/128966
PCT Pub. Date: Aug. 18, 2016

(65) Prior Publication Data
US 2018/0028604 A1    Feb. 1, 2018

Related U.S. Application Data

(60) Provisional application No. 62/114,086, filed on Feb. 10, 2015.

(51) Int. Cl.
*A61K 38/17* (2006.01)
*A61P 37/00* (2006.01)
*G01N 33/50* (2006.01)
*G01N 33/68* (2006.01)

(52) U.S. Cl.
CPC ......... *A61K 38/1709* (2013.01); *G01N 33/50* (2013.01); *G01N 33/6893* (2013.01); *G01N 2800/065* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | |
|---|---|---|
| 2012/0251539 A1 | 10/2012 | Ting et al. |
| 2015/0216929 A1 | 8/2015 | Vadasz et al. |

FOREIGN PATENT DOCUMENTS

| | | |
|---|---|---|
| WO | 2013/005603 A1 | 1/2013 |
| WO | 2014/181273 A1 | 11/2014 |
| WO | 2014/199364 A1 | 12/2014 |

OTHER PUBLICATIONS

Ponder et al., "A clinical review of recent findings in the epidemiology of inflammatory bowel disease," Clin. Epidemiol. 5:237-247 (2013) (Year: 2013).*
Müzes et al., (2012) Regulatory T cells in inflammatory bowel diseases and colorectal cancer. World J Gastroenterol 18(40): 5688-5694.
Acevedo et al., (2008) Semaphorin 3A suppresses VEGF-mediated angiogenesis yet acts as a vascular permeability factor. Blood, 111(5), 2674-2680.
Bacchetta et al., (2006) Defective regulatory and effector T cell functions in patients with FOXP3 mutations. Journal of Clinical Investigation, 116(6), 1713-1722.
Baumgart et al., (2012) Crohn's disease. The Lancet, 380(9853), 1590-1605.
Catalano et al., (2006) Semaphorin-3A is expressed by tumor cells and alters T-cell signal transduction and function. Blood, 107(8), 3321-3329.
Catalano, (2010) The neuroimmune semaphorin-3A reduces inflammation and progression of experimental autoimmune arthritis. The Journal of Immunology, 185(10), 6373-6383.
Conrotto et al., (2005) Sema4D induces angiogenesis through Met recruitment by Plexin B1. Blood, 105(11), 4321-4329.
Delaire et al., (1998) CD100 is a leukocyte semaphorin. Cellular and molecular life sciences, 54(11), 1265-1276.
Fagan et al., (1982) Serum levels of C-reactive protein in Crohn's disease and ulcerative colitis. European journal of clinical investigation, 12(4), 351-359.
Fuh et al., (2000) The interaction of neuropilin-1 with vascular endothelial growth factor and its receptor flt-1. Journal of Biological Chemistry, 275(35), 26690-26695.
Fujisawa, (2004) Discovery of semaphorin receptors, neuropilin and plexin, and their functions in neural development. Developmental Neurobiology, 59(1), 24-33.
Goodman et al., (1999) Unified nomenclature for the semaphorins/collapsins. Cell, 97(5), 551-552.
Guttmann-Raviv et al., (2007) Semaphorin-3A and semaphorin-3F work together to repel endothelial cells and to inhibit their survival by induction of apoptosis. Journal of Biological Chemistry, 282(36), 26294-26305.
Himmel et al., (2012) Regulatory T-cell therapy for inflammatory bowel disease: more questions than answers. Immunology, 136(2), 115-122.
Ikeda et al., (2000) Expression of vascular endothelial growth factor isoforms and their receptors Flt-1, KDR, and neuropilin-1 in synovial tissues of rheumatoid arthritis. The Journal of pathology, 191(4), 426-433.
Ji et al., (2009) Expression and function of semaphorin 3A and its receptors in human monocyte-derived macrophages. Human immunology, 70(4), 211-217.
Kessel et al., (2012) Human CD19+ CD25 high B regulatory cells suppress proliferation of CD4+ T cells and enhance Foxp3 and CTLA-4 expression in T-regulatory cells. Autoimmunity reviews, 11(9), 670-677.

(Continued)

*Primary Examiner* — Julie Ha
*Assistant Examiner* — Kristina M Hellman
(74) *Attorney, Agent, or Firm* — J.A. Lindeman & Co., PLLC

(57) ABSTRACT

Semaphorin 3A and uses thereof for treatment of IBD are provided. Further provided is assessing IBD severity or treatment efficacy, including determining Semaphorin 3A levels in a biological sample of a subject afflicted with IBD.

6 Claims, 4 Drawing Sheets
Specification includes a Sequence Listing.

(56) References Cited

OTHER PUBLICATIONS

Kim et al., (2006) Interaction of vascular endothelial growth factor 165 with neuropilin-1 protects rheumatoid synoviocytes from apoptotic death by regulating Bcl-2 expression and Bax translocation. The Journal of Immunology, 177(8), 5727-5735.

Kolodkin et al., (1997) Neuropilin is a semaphorin III receptor. Cell, 90(4), 753-762.

Kumanogoh et al., (2010) Semaphorins and their receptors: novel features of neural guidance molecules. Proceedings of the Japan Academy, Series B, 86(6), 611-620.

Kumanogoh et al., (2000) Identification of CD72 as a lymphocyte receptor for the class IV semaphorin CD100: a novel mechanism for regulating B cell signaling. Immunity, 13(5), 621-631.

Kumanogoh et al., (2005) Nonredundant roles of Sema4A in the immune system: defective T cell priming and Th1/Th2 regulation in Sema4A-deficient mice. Immunity, 22(3), 305-316.

Lepelletier et al., (2006) Immunosuppressive role of semaphorin-3A on T cell proliferation is mediated by inhibition of actin cytoskeleton reorganization. European journal of immunology, 36(7), 1782-1793.

Levings et al., (2002) The role of IL-10 and TGF-β in the differentiation and effector function of T regulatory cells. International archives of allergy and immunology, 129(4), 263-276.

Maul et al., (2005) Peripheral and intestinal regulatory CD4+ CD25 high T cells in inflammatory bowel disease. Gastroenterology, 128(7), 1868-1878.

Mizoguchi et al., (2006) A case for regulatory B cells. The Journal of Immunology, 176(2), 705-710.

Ordas et al., (2012) Ulcerative colitis. Lancet, 380(9853):1606-1619.

Sarris et al., (2008) Neuropilin-1 expression on regulatory T cells enhances their interactions with dendritic cells during antigen recognition. Immunity, 28(3), 402-413.

Sawaki et al., (2011) Intranasal administration of semaphorin-3A alleviates sneezing and nasal rubbing in a murine model of allergic rhinitis. Journal of pharmacological sciences, 117(1), 34-44.

Sheth et al., (2008) Diverticular disease and diverticulitis. The American journal of gastroenterology, 103(6), 1550-1556.

Staton et al., (2007) Neuropilins in physiological and pathological angiogenesis. The Journal of pathology, 212(3), 237-248.

Takahashi et al., (2008) Expression of the semaphorins Sema 3D and Sema 3F in the developing parathyroid and thymus. Developmental Dynamics, 237(6), 1699-1708.

Tordjman et al., (2002) A neuronal receptor, neuropilin-1, is essential for the initiation of the primary immune response. Nature immunology, 3(5), 477-482.

Vadasz et al., (2011) The involvement of immune semaphorins and neuropilin-1 in lupus nephritis. Lupus, 20(14), 1466-1473.

Vadasz et al., (2012) Semaphorin 3A is a marker for disease activity and a potential immunoregulator in systemic lupus erythematosus. Arthritis research & therapy, 14(3), R146, 8 pages.

Vadasz et al., (2015) The involvement of immune semaphorins in the pathogenesis of inflammatory bowel diseases (IBDs). PloS one, 10(5), e0125860, 12 pages.

Wang et al., (2011) Expression of CD4+ forkhead box P3 (FOXP3)+ regulatory T cells in inflammatory bowel disease. Journal of digestive diseases, 12(4), 286-294.

Wolf et al., (1996) Experimental autoimmune encephalomyelitis induction in genetically B cell-deficient mice. Journal of Experimental Medicine, 184(6), 2271-2278.

Yang et al., (2013) Regulatory B cells in autoimmune diseases. Cellular and Molecular Immunology, 10(2), 122-132.

\* cited by examiner

SEMAPHORIN 3A FOR TREATMENT AND ASSESSMENT OF SEVERITY OF INFLAMMATORY BOWEL DISEASE

SEQUENCE LISTING

The Sequence Listing submitted in text format (.txt) filed on Aug. 8, 2017, named "SequenceListing.txt", created on Jul. 31, 2017, 9.89 KB), is incorporated herein by reference.

FIELD OF THE INVENTION

The present invention relates to Semaphorin 3A and uses thereof for treatment of Inflammatory Bowel Disease (IBD). The invention further relates to assessing IBD severity or treatment efficacy, comprising determining Semaphorin 3A levels in a biological sample of a subject afflicted with IBD.

BACKGROUND OF THE INVENTION

Inflammatory Bowel Diseases (IBD) is a group of inflammatory conditions of the colon and small intestine. The main forms of IBD are Crohn's disease (CD) and Ulcerative Colitis (UC). Other forms of IBD, which are not always classified as typical IBD and which include far fewer cases are Collagenous colitis, Lymphocytic colitis, Ischaemic colitis, Diversion colitis, Behçet's disease, and Indeterminate colitis. The main difference between crohn's disease and UC is the location and nature of the inflammatory changes. Crohn's disease can affect any part of the gastrointestinal tract, from mouth to anus, although a majority of the cases start in the terminal ileum. UC, in contrast, is restricted to the colon and the rectum. Microscopically, UC is restricted to the mucosa (epithelial lining of the gut), while crohn's disease affects the whole bowel wall (transmural lesions). Finally, crohn's disease and UC present extra-intestinal manifestations (such as liver complications, arthritis, skin manifestations and eye complications) in different proportions.

Semaphorins are a family of membrane bound and soluble proteins classified into eight sub-classes based on their structural domains Semaphorins mainly regulate focal adhesion assembly/disassembly and induce cytoskeletal remodeling, thus affecting cell shape, cell attachment to the extracellular matrix, cell motility, and cell migration. Although Semaphorins were originally identified as affecting axon guidance during development of the nervous system, they are now thought to fulfill diverse physiological roles including organogenesis, vascularization, angiogenesis, neuronal apoptosis, and neoplastic transformation. Additionally, recent studies pointed to the involvement of Neuropilin-1 (a receptor for semaphorin 3) and certain Semaphorins in the regulation of the immune system, and thus these Semaphorins are denoted "immune Semaphorins".

The seven class-3 Semaphorins (Semaphorin 3s), designated by the letters A-G, are the only vertebrate secreted Semaphorins. Neuropilins (Nrps) and the type A/D family Plexins (Plexin-A1, -A2, and -A3, and Plexin-D1) act as receptors for Semaphorin 3. Each Semaphorin 3 family member shows distinct binding preference for Nrps. Each Sema3-Nrp complex associates with specific plexins to mediate downstream signaling. Most membrane-bound vertebrate Semaphorins directly bind plexins, while class-3 Semaphorins require Neuropilins as obligate co-receptors.

Semaphorin 3A (Sema3A), a class-3 secreted member of the Semaphorin family, has been established as an axonal guidance factor during development. Interestingly, several lines of evidence suggest that Sema3A also affects immune cell functions. Sema3A has been shown to be expressed by activated T cells and inhibit T cell proliferation and cytokine secretion (Catalano, A et al, 2006, Blood 107: 3321-3329; Lepelletier, Y. et al., 2006, Eur. J. Immunol. 36: 1782-1793). Moreover, the expression of Sema3A, Neuropilin 1 (NP-1), Neuropilin 2 (NP-2), and Plexins was found to be increased on differentiating macrophages and on activated T cells (Ji J D et al., 2009, Human Immunol., 70(4): 211-7). Additionally, Neuropilin-1 expression on regulatory T cells has been shown to enhance interactions with immature dendritic cells (DCs) during antigen recognition, resulting in higher sensitivity to limiting amounts of antigen.

One study has shown that overexpression of Sema3A in a mouse model of collagen-induced arthritis resulted in reduced incidence, disease severity, and articular inflammation. Moreover, in line with results in arthritic mice, the study showed a defective Sema3A expression in $CD4^+$ T cells derived from patients with rheumatoid arthritis (Catalano A. et al., 2010, J. Immunol., 185: 6373-83).

In another study, kidney biopsies from lupus glomerulonephritis (LGN) patients showed stronger staining with anti-NP-1, and anti-Semaphorin 3A antibodies as compared with either normal biopsies or biopsies from patients with primary nephropathy and proteinuria (Vadasz Z. et al., 2011, Lupus, 20:1466-1473). A subsequent study has shown that Sema 3A serum levels in SLE patients are significantly lower than in healthy individuals (Vadasz Z. et al, 2012, Arthritis Research & Therapy, 14:R146).

U.S. Application Publication No. 2012/0251539 discloses a method of treating an immune-related disorder in a subject, comprising administering to the subject an effective amount of a Sema3A inhibitor, resulting in reduced Sema3A activity in the subject.

International Patent Application, publication No. WO 2014/199364 to inventors of the present invention, discloses Semaphorin 3A and its use in the treatment and prognosis of Systemic Lupus Erythematosus (SLE).

US Patent Application, publication No. 2015/0216929 to inventors of the present invention, discloses Semaphorin 3A and its use in the treatment of Asthma and in assessing Asthma severity and treatment efficacy.

In yet another study, it has been shown that administration of Sema3A alleviates sneezing and nasal rubbing in a murine model of Allergic Rhinitis (Sawaki H. et al., 2011, J. Pharmacol. Sci., 117(1): 34-44).

There is an unmet need, for safe and effective approaches to treat IBD. There is also a need for reliable biomarkers with which treatment efficacy and disease condition and/or severity could be assessed.

SUMMARY OF THE INVENTION

The present invention provides methods and compositions for treatment of IBD, the methods comprising administration of a pharmaceutical composition comprising Semaphorin 3A or a derivative thereof to a subject afflicted with IBD. Further provided are methods for determining efficacy of a treatment of IBD and methods for assessing IBD condition or severity in a subject by measuring the levels of Semaphorin 3A in a biological sample(s) of an IBD patient.

The present invention is based, in part, on the unexpected discovery that the expression levels of Semaphorin 3A on T regulatory cells is significantly lower in crohn's disease patients in the active state as compared to crohn's disease patients in remission (silent state) and as compared to healthy subjects. Those findings were further supported by the observation that higher expression levels of Semaphorin 3A on T regulatory cells inversely correlated with Crohn's Disease Activity Index (CDAI). In addition, a significant lower levels of Semaphorin 3A on T regulatory cells of patients afflicted with ulcerative colitis as compared to healthy individuals was demonstrated. No significant change was indicated in the expression levels of Semaphorin 3A on regulatory B cells (CD19$^+$/CD25$^{high}$) of patients afflicted with crohn's disease as compared to healthy subjects.

Without being bound by any theory or mechanism of action, Semaphorin 3A possesses a role in regulating the immune system by affecting T regulatory cells, but not B cells. Specifically, lower levels of Sema3A on the Treg cells is associated with a reduced activity of those cells and un-hindrance induction of inflammatory response mediated by effector T cells in the intestine.

Thus, the present invention discloses, that Semaphorin 3A possesses a prominent role in modulating the immune system in IBD. Accordingly, this protein may be utilized to treat an IBD and/or assess an IBD condition, severity thereof, or progression thereof. In addition, Semaphorin 3A may be utilized as a biomarker for treatment follow-up.

According to one aspect, the present invention provides a method for treating an IBD, said method comprising administering to a subject in need thereof a pharmaceutical composition comprising a therapeutically effective amount of Semaphorin 3A, an analogue or a derivative thereof.

According to another aspect, the present invention provides a pharmaceutical composition comprising a therapeutically effective amount of Semaphorin 3A, an analogue or a derivative thereof for use in treating an IBD.

According to one embodiment, Semaphorin 3A is selected from a protein, a polypeptide, a peptide, and a nucleic acid sequence encoding an amino acid sequence of Semaphorin 3A. According to another embodiment, the Semaphorin 3A has a sequence as set forth in SEQ ID NO: 1.

According to yet another embodiment, the IBD is selected from the group consisting of: crohn's disease, and ulcerative colitis. According to yet another embodiment, the IBD is crohn's disease. According to yet another embodiment, the IBD is ulcerative colitis.

According to yet another embodiment, the pharmaceutical composition is formulated for administration via a route selected from the group consisting of: oral, rectal and intravenous.

According to yet another embodiment, administering is via a route selected from the group consisting of: oral, rectal and intravenous. Each possibility represents a separate embodiment of the invention.

According to yet another embodiment, treating results in a decrease in the Crohn's Disease Activity Index (CDAI) value of said subject.

According to another aspect, the present invention provides a method for assessing IBD severity in a subject in need thereof, said method comprising:
a) making a first measurement of Semaphorin 3A levels in a biological sample of said subject;
b) making a second measurement of Semaphorin 3A levels in a subsequent biological sample of said subject; wherein said second measurement is conducted at a later time point than said first measurement; and
c) comparing said first measurement and said second measurement; wherein an increase in Semaphorin 3A levels from the first to the second measurement is indicative of a decrease in disease severity; and wherein a decrease in Semaphorin 3A levels from the first to the second measurement is indicative of an increase in disease severity.

According to one embodiment, the biological sample is a liquid sample. According to another embodiment, the liquid sample is a blood sample. According to yet another embodiment, the blood sample is processed to produce serum, and wherein said measurements of Semaphorin 3A are determined in said serum. According to some embodiments, the biological sample is serum and the method further comprises diluting the sample.

According to yet another embodiment, Semaphorin 3A levels is Semaphorin 3A concentration in said liquid sample. According to yet another embodiment, Semaphorin 3A levels is Semaphorin 3A expression on T regulatory cells present in said liquid sample.

According to yet another embodiment, expression on T regulatory cells is percentage of T regulatory cells that express Semaphorin 3A. According to yet another embodiment, the T regulatory cells express at least one of: CD4 and CD25.

According to yet another embodiment, the increase in Semaphorin 3A expression is by at least 1.2 fold.

According to yet another embodiment, the IBD severity is selected from: intermittent, mild, moderate and severe.

According to yet another embodiment, the IBD is selected from the group consisting of: crohn's disease, and ulcerative colitis. According to yet another embodiment, the IBD is crohn's disease. According to yet another embodiment, the IBD is ulcerative colitis.

According to yet another embodiment, making a measurement of semaphorin 3A comprises determining the level of a protein, polypeptide, peptide, or nucleic acid sequence encoding an amino acid sequence of Semaphorin 3A.

According to yet another embodiment, making a measurement of semaphorin 3A comprises contacting said biological sample, with antibody directed to semaphorin 3A.

According to yet another embodiment, the method further comprising determining the presence of semaphorin 3A-antibody complex formed and quantifying the amount of semaphorin3A-antibody complex formed.

According to yet another aspect, the present invention provides a method of determining efficacy of a treatment for IBD in a subject, the method comprising:
a) making a first measurement of Semaphorin 3A levels in a first biological sample of said subject;
b) making a second measurement of Semaphorin 3A levels in a subsequent biological sample of said subject; wherein said subsequent biological sample is obtained following said subject being subjected to a treatment for IBD; and
c) comparing the levels of Semaphorin 3A in said first and second biological samples,
wherein an increase in Semaphorin 3A levels from the first to the second biological sample is indicative of said treatment being efficacious.

According to yet another aspect, the present invention provides a method of determining efficacy of a treatment for IBD in a subject, the method comprising:
a) making a first measurement of Semaphorin 3A levels in a first biological sample of said subject;
b) administering to the subject a treatment for IBD;
c) making a second measurement of Semaphorin 3A levels in a subsequent biological sample of said subject; and
d) comparing the levels of Semaphorin 3A in said first and second biological samples,
wherein an increase in Semaphorin 3A levels from the first to the second biological sample is indicative of said treatment being efficacious.

According to one embodiment, step a) is conducted prior to, or during the step of administering to the subject to a treatment for IBD. According to another embodiment, steps a) and b) are conducted during the step of administering to the subject a treatment for IBD.

According to yet another embodiment, the treatment for IBD is at least one of the treatments selected from the group consisting of: an anti-inflammatory drug, an immune system suppressor, an antibiotic, and an anti-diarrhea. According to yet another embodiment, the treatment is selected from the group consisting of: 5-aminosalicylic acid, 6-mercaptopurine, metronidazole, ciprofloxacin, azathioprine; budesonide, prednisone, and methotrexate.

According to yet another embodiment, making a measurement of semaphorin 3A comprises detecting the presence of a nucleic acid molecule expressed from the gene encoding semaphorin 3A.

According to yet another embodiment, detecting the presence of a nucleic acid molecule expressed from the gene encoding semaphorin 3A is by application of a detectably labeled probe that hybridizes to nucleic acid molecule expressed from the gene encoding semaphorin 3A.

According to yet another embodiment, the method for assessing IBD severity or determining efficacy of a treatment for IBD comprises a step of treating the subject with a pharmaceutical composition comprising a therapeutically effective amount of Semaphorin 3A.

According to yet another aspect, the present invention provides a kit for monitoring IBD severity in a subject, comprising means for making a first and a second measurement of semaphorin3A levels in a biological sample of a subject and instructions for using said kit, wherein an increase in Semaphorin 3A levels from the first to the second measurement is indicative of a decrease in disease severity; and wherein a decrease in Semaphorin 3A levels from the first to the second measurement is indicative of an increase in disease severity.

According to yet another aspect, the present invention provides a kit for determining efficacy of a treatment for IBD in a subject in need thereof, comprising means for making a first and a second measurement of semaphorin3A levels in a biological sample of a subject and instructions for using said kit, wherein an increase in Semaphorin 3A expression from the first to the second measurement is indicative of said treatment being efficacious.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
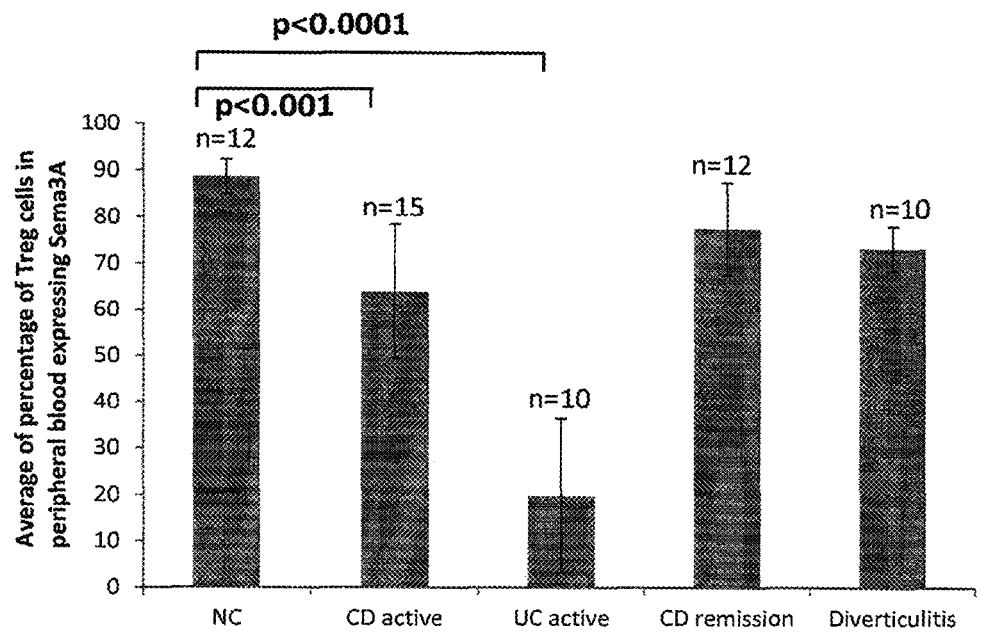
FIG. 1A is a bar graph showing the percentage of Treg cells expressing sema3A in peripheral blood in patients suffering from Crohn's disease [active (n=15) or in remission (n=12)], ulcerative colitis (active, n=10), and from patients suffering from acute diverticulitis (n=10) compared to that from healthy controls (n=12).

The present invention provides, according to one aspect, a method for treating IBD, the method comprising administering to a subject in need thereof a pharmaceutical composition comprising a therapeutically effective amount of Semaphorin 3A or a derivative thereof. According to a further aspect, the present invention provides methods of monitoring IBD based on the expression of Semaphorin 3A in a biological sample. According to yet further aspect, the present invention provides a method of determining the efficacy of a treatment to IBD based on assessing and comparing the levels of Semaphorin 3A in at least two separate biological samples, collected at distinct time points from the subject.

According to one aspect, the present invention provides methods for treating an IBD, the methods comprising administering to a subject in need thereof a pharmaceutical composition comprising a therapeutically effective amount of Semaphorin 3A, an analogue or a derivative thereof. According to some embodiments, the present invention provides a pharmaceutical composition comprising Semaphorin 3A, an analogue or a derivative thereof for use in treating an IBD in a subject in need thereof.

It is to be understood that Semaphorin 3A is interchangeable with any alternative name or synonym of this protein known in the art. Typical semaphorin-3A synonyms include, but are not limited to, collapsin 1, semaphorin III and Sema 3A.

As used herein the term "Inflammatory bowel disease" (IBD) refers to a disease which involves chronic inflammation of all or part of the digestive tract. The term includes all kind of IBD known in the art. IBD primarily includes ulcerative colitis and Crohn's disease, but additional IBDs are known and include, without limitation, Collagenous colitis, Lymphocytic colitis, Ischaemic colitis, Diversion colitis, Behçet's disease, and Indeterminate colitis. Each possibility represents a separate embodiment of the invention.

Ulcerative Colitis (UC) is characterized in long-lasting inflammation in part of the digestive tract. Symptoms usually develop over time, rather than suddenly. Ulcerative colitis typically affects only the innermost lining of the large intestine (colon) and rectum. It occurs through continuous stretches of the colon. Ulcerative colitis is categorized to: ulcerative proctitis, proctosigmoiditis, left-sided colitis, pancolitis, and fulminant colitis. This classification is based on the signs/symptoms of the disease. It is to be understood that each of the aforementioned forms of UC are included within the scope and represent a separate embodiment of the present invention.

Ulcerative proctitis is characterized in inflammation that is confined to the area closest to the anus (rectum), and in some patients, rectal bleeding may be the only sign of the disease. This form of ulcerative colitis tends to be the mildest in terms of disease severity. Proctosigmoiditis involves the rectum and the lower end of the colon (sigmoid colon). Left-sided colitis involves inflammation that extends from the rectum up through the sigmoid and descending colon, which are located in the upper left part of the abdomen. Pancolitis affects more than the left colon and often the entire colon. Fulminant colitis is a rare, life-threatening form of colitis that affects the entire colon and causes severe pain, profuse diarrhea and, sometimes, dehydration and shock. People with fulminant colitis are at risk of serious complications, including colon rupture and toxic megacolon, a condition that causes the colon to rapidly expand. The course of ulcerative colitis varies, with periods of acute illness often alternating with periods of remission. Most people with a milder condition, such as ulcerative proctitis, won't go on to develop more-severe signs and symptoms.

Overall UC symptoms include, but are not limited to, abdominal pain, bloody diarrhea with mucus, tiredness, fatigue, appetite loss, weight loss, anemia, a high temperature (fever), dehydration, and a constant desire to empty the bowels (known as tenesmus).

Crohn's disease is characterized in inflammation present along the lining of the digestive tract, and often spreads deep into affected tissues. This can lead to abdominal pain, severe diarrhea and even malnutrition. The inflammation caused by Crohn's disease can involve different areas of the digestive tract in different people. The most common areas affected by Crohn's disease are the last part of the small intestine called the ileum and the colon. Inflammation may be confined to the bowel wall, which can lead to scarring (stenosis), or inflammation may spread through the bowel wall (fistula). Signs and symptoms of Crohn's disease can range from mild to severe and may develop gradually or come on suddenly, without warning. Signs and symptoms include, without limitation, diarrhea, abdominal pain and cramping, nausea and vomiting, blood in the stool, ulcers on the surface of the intestine or in the mouth, reduced appetite and weight loss, fever, fatigue, arthritis, eye inflammation, skin disorders, inflammation of the liver or bile ducts, and delayed growth or sexual development (in children). In CD, increased Th1 and Th17 cell activation is an important factor in inducing the inflammation in bowel lamina propria. Both types of T effector cells do react to bacterial bowel antigens when primary local immune responses fail to eliminate these antigens, and were therefore, found to be continuously exposed to adaptive immune responses. This situation leads to the intensive and continuous production of pro-inflammatory cytokines such as Th1 mediated ones, namely Interleukin (IL)-1, IL-6, TNF, and others.

As used herein the term "T regulatory cells" is interchangeable with the terms "Treg", "regulatory T cells" and "suppressor T cells". T regulatory cells refer to a subpopulation of T cells which modulate the immune system, maintain tolerance to self-antigens, and abrogate autoimmune disease. Those Treg cells can either be naturally occurring or induced by the conversion of naive T cells in the presence of TGF-beta. Regulatory T cells may be detected by markers. The most well-understood and known Treg cells are those that express CD4 (CD4+) and CD25 (CD25+). Foxp3 can be used as a marker for mouse and human CD4+CD25+ T cells, although recent studies have also shown evidence for Foxp3 expression in CD4+CD25− T cells. Foxp3 is a prominent regulator of T cells known to possess suppressive effect on TH1 and TH2 cells and thereby to inhibit inflammation. An additional Treg population includes cells expressing Tr1, Th3, CD8+CD28+, and Qa-1. The contribution of this population to self-tolerance and immune homeostasis is less well defined.

As used herein, the term "treating" includes, but is not limited to, any one or more of the following: abrogating, ameliorating, inhibiting, attenuating, blocking, suppressing, reducing, delaying, halting, alleviating or preventing symptoms associated with IBD, and/or IBD related pathology and condition. The methods of the present invention encompass patients having persistent symptoms as well as patients that rarely experience symptoms. Each possibility represents a separate embodiment of the present invention.

According to some embodiments, a subject in need thereof is a subject afflicted with an IBD or a subject having complications associated with IBD. The term "subject" is interchangeable with the term "patient" or "individual". The subject may be a human subject. Alternatively, the subject may be a mammal According to some embodiments, the subject is symptomatic. According to some embodiments, the subject is asymptomatic.

According to some embodiments, a therapeutically effective amount refers to an amount sufficient to induce a decrease in an IBD disease activity or severity. According to some embodiments, the IBD is crohn's disease and the activity or severity is assessed according to Crohn's Disease Activity Index (CDAI). In accordance with this embodiment, a therapeutically effective amount of sema 3A refers to an amount sufficient to reduce the CDAI in a patient. According to some embodiments, a therapeutically effective amount refers to an amount sufficient to increase the serum concentration of sema3A of a subject. According to some embodiments, a therapeutically effective amount refers to an amount sufficient to increase the percentage of Treg cells expressing Semaphorin 3A in a biological sample of a subject to be at least 80% or at least 90% of the Treg cells. Each possibility represents a separate embodiment of the invention. According to some embodiments, a therapeutically effective amount refers to an amount sufficient to ameliorate and/or prevent at least one of the symptoms associated with IBD.

According to some embodiments, the method of treating an IBD with sema3A further comprises an additional treatment of IBD other than the treatment of the present invention. According to some embodiments, the additional treatment may be provided before, after, or concomitantly with the administration of the pharmaceutical compositions comprising the Semaphorin 3A. According to some embodiments, treating IBD according to the present invention comprises administration of a pharmaceutical composition comprising Semaphorin 3A and an additional agent/medicament/drug.

Treatments for IBD aim at reducing the inflammation associated with the disease. IBD treatment typically involves either drug therapy or surgery. Drug therapy typically includes, but is not limited to, an anti-inflammatory drug, an immune system suppressor, an antibiotic, and an anti-diarrhea drug. Each possibility represents a separate embodiment of the invention.

Suitable anti-inflammatory drugs may include, but are not limited to, Sulfasalazine (e.g., Azulfidine®), Mesalamine (e.g., Apriso®, Asacol®, and Lialda®), Balsalazide (e.g., Colazal), and Olsalazine (e.g., Dipentum®). Also classified as anti-inflammatory drugs are corticosteroids. Corticosteroids are effective in reducing inflammation, but they have numerous side effects, and hence are not recommended for long-term use. Common side effects of corticosteroids include weight gain, excessive facial hair, mood swings, high blood pressure, and an increased susceptibility to infections. Corticosteroids are usually prescribed if the IBD disease is moderate to severe and hasn't responded to other treatments.

Immune system suppressors target the immune system rather than treating inflammation itself. Immune system suppressors are associated with a small risk of developing cancer, such as lymphoma. Immunosuppressant drugs include, but are not limited to, Azathioprine (e.g., Azasan, Imuran), Mercaptopurine (e.g., Purinethol®), Cyclosporine (e.g., Gengraf®, Neoral®, Sandimmune®), Infliximab (e.g., Remicade®), Adalimumab (e.g., Humira®), Certolizumab pegol (e.g., Cimzia®), Methotrexate (e.g., Rheumatrex®), Natalizumab (e.g., Tysabri®), Adalimumab (e.g., Humira®), and Natalizumab (e.g., Tysabri®).

Infliximab is usually prescribed to patients afflicted with moderate to severe ulcerative colitis who don't respond to or can't tolerate other treatments. Infliximab mechanism of action is neutralization of tumor necrosis factor (TNF). Adalimumab works similarly to infliximab by blocking TNF and is prescribed mainly to patients afflicted with moderate to severe crohn's disease. Adalimumab, like infliximab, carries a small risk of complications, including tuberculosis and serious fungal infections. The most common side effects of adalimumab are skin irritation and pain at the injection site, nausea, runny nose and upper respiratory infection. Certolizumab pegol (Cimzia®) is approved by the Food and Drug Administration for the treatment of Crohn's disease. This drug also inhibits TNF. Certolizumab pegol is prescribed for patients with moderate to severe Crohn's disease. Methotrexate (Rheumatrex®) is primarily used to treat cancer, psoriasis and rheumatoid arthritis. Methotrexate is prescribed for crohn's disease in cases where the patient hasn't responded well to other medications. Natalizumab (Tysabri®) inhibits integrins and thereby interferes binding of cells to the intestines. Natalizumab is approved for people with moderate to severe crohn's disease with evidence of inflammation and who aren't responding well to other conventional crohn's disease therapies. Antibiotics can reduce the amount of drainage and sometimes heal fistulas and abscesses in people with crohn's disease. Researchers also believe antibiotics help reduce harmful intestinal bacteria and suppress the intestine's immune system, which can trigger symptoms. Frequently prescribed antibiotics include, Metronidazole (Flagyl®), and Ciprofloxacin (Cipro®).

In addition to controlling inflammation, some medications may help relieve the signs and symptoms. Those medications include, without limitation, anti-diarrheas such as psyllium powder (Metamucil®), Methylcellulose (Citrucel®) and Loperamide (Imodium®), Laxatives (to assist in lowering swelling), pain relievers, iron supplements (to assist in cases where the IBD is associated with iron deficiency anemia), Vitamin B-12 (to prevent anemia), calcium and vitamin D supplements.

The aforementioned various agents used to treat IBD may be combined with the sema3A treatment of the invention. Thus, according to some embodiments of the invention, the composition comprising Sema3A further comprises a drug selected from the group consisting of: an anti-inflammatory drug, an immune system suppressor, an antibiotic, and an anti-diarrhea and a combination thereof. Each possibility represents a separate embodiment of the present invention. According to some embodiments, the drug is selected from the group consisting of: 5-aminosalicylic acid, 6-mercaptopurine, metronidazole, ciprofloxacin, azathioprine; budesonide, prednisone, and methotrexate. Each possibility represents a separate embodiment of the present invention.

According to some embodiments, treatment of IBD comprises a surgery. In UC, surgery often eliminates the disease. Surgery is typically associated with removing the entire colon and rectum (proctocolectomy). In crohn's disease, surgery may provide years of remission at best. At the least, it may provide a temporary improvement in the signs and symptoms. Surgery is typically associated with removal of a damaged portion of the digestive tract which follows with reconnection of the healthy sections. In addition, surgery may also be used to close fistulas and drain abscesses. A common procedure for crohn's is strictureplasty, which widens a segment of the intestine that has become too narrow. According to some embodiments of the invention, a method of treating an IBD with a composition comprising Sema3A may further include surgery.

According to some embodiments, treatment with Semaphorin 3A comprises administration of Sema3A peptide, polypeptide or protein. The semaphorin 3A may be natural or a variant or an analogue. According to some embodiments, Semaphorin 3A, its analogue or derivative is a recombinant protein, polypeptide or peptide.

According to some embodiments, treatment with Semaphorin 3A comprises administration of a polynucleotide sequence encoding sema3A peptide, polypeptide or protein. According to some embodiments, treatment with Semaphorin 3A comprises administration of a polynucleotide sequence that induces, controls or regulates sema3A translation within a target cell/tissue.

According to some embodiments, treatment with Semaphorin 3A comprises administering living cells genetically engineered to express high levels of sema 3A. This type of therapy is known as cell therapy. In one form of cell therapy, the cells that are implanted have been genetically modified in vitro with exogenous genetic material so as to enable the cells to produce a desired biological substance that is useful as a therapeutic agent. Methods of genetically engineering cells are known to those skilled in the art. Methods for implantation or transplantation of Sema 3A secreting cells include encapsulation of the cells in any immunologically inert matrix including gelatin or polymers.

According to some embodiments, Semaphorin 3A, analogue or derivative is from a mammalian origin. According to some embodiments, Semaphorin 3A is an isolated Semaphorin 3A. According to some embodiments, Semaphorin 3A its analogue or derivative is from a human origin. According to some embodiments, Semaphorin 3A as used herein is a human Semaphorin 3A having an amino-acid sequence as set forth in SEQ ID NO: 1, or a fragment thereof. The polynucleotide sequence as set forth in SEQ ID NO: 2 corresponds to the cDNA encoding human Semaphorin 3A as set forth in SEQ ID NO: 1.

According to some embodiments, Semaphorin 3A derivative may be a fragment or an analogue of a naturally occurring Semaphorin 3A that exhibits substantial identical functionality to the naturally occurring Semaphorin 3A. According to some embodiments, Semaphorin 3A derivative or analogue refers to a polypeptide having at least 70%, at least 80% or at least 90% homology to the naturally occurring Semaphorin 3A. Each possibility represents a separate embodiment of the invention. According to some embodiments, homology is interchangeable with identity. According to some embodiments, Semaphorin 3A derivative or analogue refers to a polypeptide that has at least 70%, at least 80% or at least 90% the functionality of the naturally occurring Semaphorin 3A. Each possibility represents a separate embodiment of the invention.

According to some embodiments, Semaphorin 3A further comprises a protein tag. According to some embodiments, Semaphorin 3A comprises a protein tag upon production but the tag is cleaved and/or removed from Semaphorin 3A prior to incorporation into the composition of the invention. Cleavage and/or removal of a tag may be performed by any method known in the art, such as, but not limited to, enzymatic and/or chemical cleaving, so long Semaphorin 3A remains functional. According to some embodiments, functional Semaphorin3A refers to Semaphorin 3A which is able to reduce IBD activity and/or ameliorate at least one of IBD symptoms. Each possibility represents a separate embodiment of the present invention.

As used herein, the term "protein tag" refers to a peptide sequence bound to the N-terminus or C-terminus of a protein. According to some embodiments, a protein tag may comprise a glycoprotein. According to some embodiments, a protein tag may be used for separation and/or purification of the bound protein. Each possibility represents a separate embodiment of the present invention. Non-limiting examples of protein tags are: Myc, Human influenza hemaglutinin (HA), Flag, His, Gluthathione-S-Transferase (GST) and a combination thereof. Each possibility represents a separate embodiment of the present invention.

As used herein, the term "isolated" means either: 1) separated from at least some of the components with which it is usually associated in nature; 2) prepared or purified by a process that involves the hand of man; and/or 3) not occurring in nature.

According to some embodiments, isolated Semaphorin 3A, as disclosed herein may be produced by recombinant or chemical synthetic methods. According to some embodiments, Semaphorin 3A as disclosed herein may be produced by recombinant methods from genetically-modified host cells. Any host cell known in the art for the production of recombinant proteins may be used for the present invention. According to some embodiments, the host cell is a prokaryotic cell. Representative, non-limiting examples of appropriate prokaryotic hosts include bacterial cells, such as cells of *Escherichia coli* and *Bacillus subtilis*. According to other embodiments, the host cell is a eukaryotic cell. According to some exemplary embodiments, the host cell is a fungal cell, such as yeast. Representative, non-limiting examples of appropriate yeast cells include *Saccharomyces cerevisiae* and *Pichia pastoris*. According to additional exemplary embodiments, the host cell is a plant cell.

Following are non-limiting examples of recombinant and chemical synthetic methods suitable for production of Semaphorin 3A, according to the present invention.

Recombinant Expression

As used herein, the term "gene" has its meaning as understood in the art. In general, a gene is taken to include gene regulatory sequences (e.g. promoters, enhancers, etc.) and/or intron sequences, in addition to coding sequences (open reading frames).

As used herein, the terms "polypeptide" and "protein" are used interchangeably and refer to a polymer of amino acid residues.

As used herein, the term "DNA construct" refers to an artificially assembled or isolated nucleic acid molecule which comprises a gene of interest or a coding region of interest. According to some embodiments, a gene of interest is a gene encoding human Semaphorin 3A. According to some embodiments, a coding region of interest is a coding region encoding Semaphorin 3A. According to some embodiments, a coding region of interest is a coding region encoding for human Semaphorin 3A as set forth in SEQ ID NO:2.

As used herein, the term "vector" refers to any recombinant polynucleotide construct (such as a DNA construct) that may be used for the purpose of transformation, i.e. the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced.

As used herein, a "primer" defines an oligonucleotide which is capable of annealing to (hybridizing with) a target nucleotide sequence, thereby creating a double stranded region which can serve as an initiation point for DNA synthesis under suitable conditions.

As used herein, the terms "transformation" or "transfection" refers to the introduction of foreign DNA into cells. The terms "transformants", "transformed cells", or "transfected cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

Semaphorin 3A may be synthesized by expressing a polynucleotide molecule encoding Semaphorin 3A in a host cell, for example, a microorganism cell transformed with the nucleic acid molecule.

DNA sequences encoding wild type polypeptides, such as Semaphorin 3A, may be isolated from any cell producing them, using various methods well known in the art. For example, a DNA encoding the wild-type polypeptide may be amplified from genomic DNA by polymerase chain reaction (PCR) using specific primers, constructed on the basis of the nucleotide sequence of the known wild type sequence.

The genomic DNA may be extracted from the cell prior to the amplification using various methods known in the art.

The isolated polynucleotide encoding the wild type polypeptide may be cloned into any vector known in the art.

Upon isolation and cloning of the polynucleotide encoding the wild type polypeptide, desired mutation(s) may be introduced by modification at one or more base pairs, using methods known in the art, such as for example, site-specific mutagenesis, cassette mutagenesis, recursive ensemble mutagenesis and gene site saturation mutagenesis. Methods are also well known for introducing multiple mutations into a polynucleotide. For example, introduction of two and/or three mutations can be performed using commercially available kits.

An alternative method to producing a polynucleotide with a desired sequence is the use of a synthetic gene. A polynucleotide encoding a desired polypeptide may be prepared synthetically, for example using the phosphoroamidite method.

The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type.

In the case of a fusion protein, or a protein fused with a protein tag, different polynucleotides may be ligated to form one polynucleotide. The polynucleotide encoding the polypeptide of the invention, such as, but not limited to the polynucleotide encoding human Semaphorin 3A (SEQ ID NO:2), may be incorporated into a wide variety of expression vectors, which may be transformed into in a wide variety of host cells.

Introduction of a polynucleotide into the host cell can be effected by well-known methods, such as chemical transformation (e.g. calcium chloride treatment), electroporation, conjugation, transduction, calcium phosphate transfection, DEAE-dextran mediated transfection, transvection, microinjection, cationic lipid-mediated transfection, scrape loading, ballistic introduction and infection.

Representative, non-limiting examples of appropriate hosts include bacterial cells, such as cells of *E. coli* and *Bacillus subtilis*.

The polypeptides may be expressed in any vector suitable for expression. The appropriate vector is determined according to the selected host cell. Vectors for expressing proteins in *E. coli*, for example, include, but are not limited to, pET, pK233, pT7 and lambda pSKF. Other expression vector systems are based on betagalactosidase (pEX); maltose binding protein (pMAL); and glutathione S-transferase (pGST).

The polypeptides may be designed to include a protein tag, for example, a His-Tag (six consecutive histidine residues), which can be isolated and purified by conventional methods.

Selection of a host cell transformed with the desired vector may be accomplished using standard selection protocols involving growth in a selection medium which is toxic to non-transformed cells. For example, in the case of *E. coli*, it may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the polypeptide may be identified in cell extracts of the transformed cells. Transformed hosts expressing the polypeptide may be identified by analyzing the proteins expressed by the host, for example, using SDS-PAGE and comparing the gel to an SDS-PAGE gel obtained from the host which was transformed with the same vector but not containing a nucleic acid sequence encoding the desired polypeptide.

The desired polypeptides which have been identified in cell extracts may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof. The polypeptides of the invention may be produced as fusion proteins, attached to an affinity purification protein tag, such as a His-tag, in order to facilitate their rapid purification.

The isolated polypeptide may be analyzed for its various properties, for example specific activity, using methods known in the art. In a non-limiting example, isolated Semaphorin 3A may be analyzed for its ability to increase expression of Foxp3 on $CD25^+/CD4^+$ Treg cells isolated from IBD patients.

Conditions for carrying out the aforementioned procedures as well as other useful methods are readily determined by those of ordinary skill in the art.

Semaphorin 3A according to the present invention may also be produced by synthetic means using well known techniques, such as solid phase synthesis. Synthetic polypeptides may be produced using commercially available laboratory peptide design and synthesis kits. In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

As presented in the experimental section that follows, the expression of Semaphorin 3A on Treg cells of healthy subjects and of patients afflicted with crohn's disease in remission/silent state is significantly higher than on Treg cells of patients with active crohn's disease. Likewise, Semaphorin 3A expression on T regulatory cells is inversely correlated with crohn's disease activity measured using CDAI.

Also, the expression of Semaphorin 3A on Treg cells of patients afflicted with active ulcerative colitis is significantly lower as compared to healthy subjects.

Thus, according to another aspect, the present invention provides a method for assessing IBD severity in a subject in need thereof, the method comprising:
a) making a first measurement of Semaphorin 3A or a derivative thereof levels in a biological sample of said subject;
b) making a second measurement of Semaphorin 3A or a derivative thereof levels in a subsequent biological sample of said subject; wherein said second measurement is conducted at a later time point than said first measurement; and
c) comparing said first measurement and said second measurement; wherein an increase in Semaphorin 3A levels from the first to the second measurement is indicative of a decrease in disease severity; and wherein a decrease in Semaphorin 3A levels from the first to the second measurement is indicative of an increase in disease severity.

In this context the term "derivative thereof" encompasses any form of naturally occurring semaphorin 3A and includes splice variants of semaphorin 3A, or mutant forms of semaphorin 3A. Mutant forms of semaphorin 3A include truncated, or point mutated forms of semaphorin 3A.

As used herein the term "semaphorin 3A levels" refers to either the amount of Sema3A mRNA or protein in a biological sample or expression in cells present in the biological sample. Each possibility represents a separate embodiment of the invention. According to some embodiments, Semaphorin 3A expression denotes assessment of the levels of this protein expressed in cell(s) in a biological sample. According to some embodiments, levels of expression may be assessed in a plurality of cells present in a biological sample without particularly assessing the expression in a specific cell type. According to some embodiments, levels of expression may be assessed in a particular cell type. According to one embodiment, sema 3A levels is Sema 3A expression on Treg cells present in a biological sample of a subject. According to some embodiments, measurement of Sema 3A expression on cells (e.g., Treg cells) include determining the percentage of cells that express Semaphorin 3A. According to alternative embodiments, measurement of Sema 3A expression on cells include measuring the intensity of sema 3A expression on the cells that express this protein. According to some embodiments, Semaphorin 3A levels is concentration of this protein, peptide or polypeptide in a fluid biological sample.

As used herein, the term "Semaphorin 3A levels" encompasses measurements of amount (concentration or total amount) or of arbitrary units. "Arbitrary units" are usually measured in methodologies such as fluorescence spectroscopy, Fluorescence Activated Cells Sorter (FACS), or densitometry of western/northern blotting. The term "concentration" refers to the abundance of a constituent divided by the total volume of a mixture.

As used herein the term "assessing IBD severity" refers to evaluating, determining or classifying IBD condition in a subject. According to some embodiments, the method of "determining IBD severity" comprises classifying the severity of the disease according to a particular method of grading.

Crohn's Disease Activity Index (CDAI) is a research tool used to quantify the symptoms of patients with crohn's disease. This tool is of particular importance in order to define response or remission of the disease following treatment with a medication/drug. The index consists of eight factors, each summed following adjustment with a weighting factor. The factors of the CDAI and their relative weight in calculating the overall score are as follows: number of liquid or soft stools each day for seven days (weighting factor X2), abdominal pain (graded from 0-3 on severity) each day for seven days (weighting factor X5), general well being (subjectively assessed from 0=well to 4=terrible) each day for seven days (weighting factor X7), presence of complications (weighting factor X20), taking lomotil or opiates for diarrhea (weighting factor X30), presence of an abdominal mass (0 as none, 2 as questionable, 5 as definite) (weighting factor X10), hematocrit of <0.47 in men and <0.42 in women (weighting factor X6), and percentage deviation from standard weight (weighting factor X1). Complications include the presence of joint pains (arthralgia) or frank arthritis, inflammation of the iris or uveitis, presence of erythema nodosum, pyoderma gangrenosum, or aphthous ulcers, anal fissures, fistulae or abscesses, other fistulae, fever during the previous week. Each of those complications mentioned hereinabove is considered equally. Typically, remission of crohn's disease is defined as CDAI below 150 and severe disease is defined as a value of greater than 450. Most major research studies on medications in crohn's disease define response as a fall of the CDAI of greater than 70 points.

Ulcerative colitis activity is assessed using the "Mayo score" or the "Disease Activity Index" (DAI). The mayo score ranges from 0 to 12, with higher scores indicating more severe disease. This score can be used for both initial evaluation and monitoring treatment response. The mayo score takes into account the following parameters: stool frequency, rectal bleeding, endoscopic findings, and physician's global assessment. The physician's global assessment ranges from normal, mild, moderate and severe. Typically, points of 0-1 are designated as normal or denote no active disease, points of 2 to 5 denote mild disease, and points 6 to 12 denote moderate to severe disease.

As used herein the term "biological sample" refers to any sample obtained from the subject being tested. According to some embodiments, the biological sample is selected from: cells, tissue and bodily fluid. Each possibility represents a separate embodiment of the invention. According to some embodiments, the biological sample is a solid or a tissue sample. According to some embodiments, the solid sample or tissue sample is obtained from the colon or the small intestine. According to some embodiments, the biological sample is a fluid sample. According to some embodiments, the fluid sample is selected from the group consisting of: whole blood, plasma, and serum. Each possibility represents a separate embodiment of the invention. According to one embodiment, the fluid sample is a serum sample.

The biological sample is obtained or collected from the subject in any method known in the art. The sample may be collected from the subject by noninvasive, invasive or minimal invasive means. Each possibility represents a separate embodiment of the invention.

According to some embodiments, the sample may be treated prior to being subjected to measuring sema3A levels. According to some embodiments, the sample is serum and is therefore substantially free of cells or debris of cells.

As used herein the term "serum" refers to the component in blood that does not contain white or red blood cells nor clotting factors. Serum includes all proteins not used in blood clotting (coagulation) and all the electrolytes, antibodies, antigens, hormones, and any exogenous substances (e.g., drugs and microorganisms). Typically, for preparing serum, a whole blood sample collected from a patient is inserted into an appropriate tube. Then the whole blood sample is left at room temperature for at least 15 minutes to allow the blood to clot. The clot is removed by centrifuging (for example at 1,000-2,000×g for 10 minutes). The resulting supernatant is designated serum. According to some embodiments, the clotting procedure is conducted by leaving the blood sample at room temperature for at least 30 minutes, or for an hour. Each possibility represents a separate embodiment of the invention. For obtaining plasma from a whole blood sample, the whole blood collected is inserted to commercially available anticoagulant-treated tube (e.g., EDTA-treated or citrate-treated tube). Cells are removed from plasma by centrifugation (for example at 1,000-2,000×g 10 minutes). Centrifugation for 15 minutes at 2,000×g depletes platelets in the plasma sample. The resulting supernatant is designated plasma. According to some embodiments, the liquid (e.g., serum) sample is diluted prior to analysis of sema3A concentration. According to some embodiments, the sample is diluted 1:5, 1:10, 1:20, or 1:100 using, for example, PBS or saline. Each possibility represents a separate embodiment of the present invention. According to one embodiment, the sample is diluted 1:50. Alternatively, the sample may undergo concentration with a suitable membrane pore cut-off size of, for example, 5,000, 10,000, 30,000 or 50,000 kDa is used. Each possibility represents a separate embodiment of the present invention.

According to additional embodiments, the sample may conveniently be frozen after being collected from the subject or after being subjected to a preparation procedure and thawed before determining the levels of semaphorin 3A, e.g. by an immunoassay.

According to some embodiments, the sample is selected from the group consisting of formalin-fixed paraffin-embedded (FFPE) tissue, fresh frozen (FF) tissue, and tissue comprised in a solution that preserves nucleic acid or protein molecules. Each possibility represents a separate embodiment of the invention.

It should be noted that a "biological sample obtained from the subject" may also optionally comprise a sample that has not been physically removed from the subject.

According to some embodiments, a decrease in IBD disease activity or severity is characterized by amelioration of at least one of the symptoms of IBD. According to some embodiments, an increase in IBD disease activity is characterized by worsening or appearance of at least one symptom of IBD.

According to some embodiments, "an increase" or "decrease" in Semaphorin 3A levels from the first to the second measurement" refers to relative differences, which may be statistically significant, or in some embodiments, when viewed as a whole or over a prolonged period of time, etc., indicate a trend in terms of differences in Semaphorin 3A levels.

According to some embodiments, "an increase in Semaphorin 3A levels from the first to the second measurement" refers to an increase in the percentage of Treg cells that express Semaphorin 3A such that the second measurement will provide a value of about 80% or 90% or above of the T reg cells that express Semaphorin 3A. According to some embodiments, "an increase in Semaphorin 3A expression from the first to the second measurement" is an increase of at least 1.2, 1.3, 1.4, 1.5, 1.6, 1.7, 1.8, 1.9, 2, 3, 4, or 5 fold from the second to the first measurement. Each possibility represents a separate embodiment of the present invention. According to some embodiments, "an increase in Semaphorin 3A expression from the first to the second measurement" is an increase by at least 10%, at least 20%, at least 30%, at least 40%, at least 50%, at least 60%, at least 70% or at least 80% from the second to the first measurement. Each possibility represents a separate embodiment of the present invention.

According to some embodiments, the term "about" as used herein refers to +/−10 of the indicated values.

According to some embodiments, measurement of serum Semaphorin 3A concentration or expression on T regulatory cells may be performed by any method known in the art. According to some embodiments, measurement of serum or T regulatory cells Semaphorin 3A is performed on a sample obtained from a subject in need thereof. According to some embodiments, the sample is a blood sample. According to some embodiments, Semaphorin 3A can be detected and quantified by any of a number of methods well known to those of skill in the art. These may include, but are not limited to, analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as, but not limited to, fluid or gel precipitin reactions, immunodiffusion (single or double), immunohistochemistry, affinity chromatography, immunoelectrophoresis, radioimmunoassay (RIA), enzyme-linked immunosorbent assay (ELISA), immunofluorescent assay, Western blotting, Fluorescence Activated Cell Sorter (FACS) and the like. According to some embodiments, measurement of serum Semaphorin 3A is performed using an enzyme-linked immunosorbent assay (ELISA).

According to some embodiments, the method of the invention comprises a step of administering to the subject a treatment for IBD. In accordance of those embodiments, an increase in Semaphorin 3A levels from the first to the second measurement is indicative of said treatment being efficacious.

According to some embodiments, the term "at a later time point" refers to any time point in between or after 1, 2, 3, 4, 5, 6, 7, 14, 21, 30, 60, or 90 days from the first measurement. Each possibility represents a separate embodiment of the invention.

It is to be understood that the sema3A measurements of steps a) and b) are conducted on separate distinct biological samples taken at two different time points.

According to some embodiments, the first measurement is taken as close as possible prior to the beginning of the IBD treatment, preferably within a day of the beginning of treatment. According to some embodiments, the first measurement is taken at the time of diagnosing a subject with IBD or as close as possible to the time of said diagnosis. Each possibility represents a separate embodiment of the present invention. According to some embodiments, the second measurement is taken following termination of the treatment. According to some embodiments, the second measurement is taken in the course of treatment with the IBD treatment. According to some embodiments, the second measurement is taken at least 1, 2, 3, 4, 5, 6, 7, 14, 21, 30, 60, or 90 days after the beginning of the treatment. Each possibility represents a separate embodiment of the present invention. According to some embodiments, the second measurement is taken at least a week after the beginning of the IBD treatment. According to some embodiments, the second measurement is taken at least 1, 2, 3, 4, 5, 6, 7, 14, 21, 30, 60, or 90 days following termination of the IBD treatment. Each possibility represents a separate embodiment of the present invention. According to some embodiments, the second measurement is taken at least a week following termination of the IBD treatment.

According to some embodiments, treatment for IBD may be any treatment mentioned in hereinabove. According to some embodiments, treatment for IBD is at least one of the treatments selected from the group consisting of: an anti-inflammatory drug, an immune system suppressor, an antibiotic, and an anti-diarrhea. According to some embodiments, the treatment is selected from the group consisting of: 5-aminosalicylic acid, 6-mercaptopurine, metronidazole, ciprofloxacin, azathioprine; budesonide, prednisone, and methotrexate.

It is to be noted that, the increase in Semaphorin 3A serum concentration and/or expression on T regulatory cells following treatment according to the present invention is dependent on the specific physiological parameters of each subject. Therefore, treatment according to the embodiments of the present invention may result in a different increase in Semaphorin 3A concentration in a serum or expression on T regulatory cells of a subject. For example, an increase in serum concentration of Semaphorin 3A or expression on T regulatory cells of about 10% may be accounted as treating according to certain embodiments of the invention.

The methods of the invention are useful for "managing subject treatment" by the clinician or physician subsequent to the determination of treatment efficacy or severity of the disease state. For example, if the severity of the IBD indicates that surgery is appropriate, the physician may schedule the patient for surgery. Furthermore, if the results show that treatment has been successful, no further management may be necessary. Alternatively, if the result of the methods of the present invention is inconclusive or there is reason that confirmation of status is necessary, the physician may order more tests.

Therapeutic Use

According to an aspect of the invention, there is provided a pharmaceutical composition comprising Sema3A, an analogue or a derivative thereof for use in treating an IBD.

The pharmaceutical composition comprising Sema3A may be administered to a subject by any suitable route of administration, including but not limited to, local and systemic routes. Exemplary suitable routes of administration include, but are not limited to: orally, intravenously, rectal. According to another embodiment, systemic administration of the composition is via an injection. For administration via injection, the composition may be formulated in an aqueous solution, for example in a physiologically compatible buffer including, but not limited, to Hank's solution, Ringer's solution, or physiological salt buffer. Formulations for injection may be presented in unit dosage forms, for example, in ampoules, or in multi-dose containers with, optionally, an added preservative.

According to another embodiment, administration systemically is through a parenteral route. According to some embodiments, parenteral administration is administration intravenously, intra-arterially, intramuscularly, intraperitoneally, intradermally, intravitreally, or subcutaneously. Each of the abovementioned administration routes represents a separate embodiment of the present invention. According to another embodiment, parenteral administration is performed by bolus injection. According to another embodiment, parenteral administration is performed by continuous infusion. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to another embodiment, administration systemically is through an enteral route. Suitable enteral administration routes include, but are not limited to, oral administration and rectal administration. Suitable dosage forms for rectal administration include, but are not limited to, ointment, suppository, enema (solution or hydrogel), murphy drip and nutrient enema.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin, for use in a dispenser may be formulated containing a powder mix of the composition of the invention and a suitable powder base, such as lactose or starch.

Solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

Example 1: An Inverse Correlation Between Semaphorin 3A Expression on T Regulatory Cells and IBD Activity A prospective study was conducted on individuals at various stages of bowel diseases. Blood samples were obtained from the following groups: (a) patients with active Crohn's (n=15); (b) patients with crohn's disease in remission (silent) (n=12); (c) patients with active ulcerative colitis (n=10); (d) patients with acute diverticulitis (n=10); and (e) healthy individuals (control, n=12). All patients were in routine follow-up at the Department of Gastroenterology in Bnai-Zion Medical Center. Blood was drawn from all participants and biopsies were performed at disease onset.

In addition, serum C-reactive protein (CRP) test which measures general levels of inflammation in the body was assessed. Crohn's disease activity was assessed and defined using the CD activity index (CDAI). Remission of Crohn's disease was defined as CDAI of below 220. Active Crohn's disease was defined as CDAI of above 220. Ulcerative colitis activity was assessed and defined according to Mayo score. Active UC was defined as Mayo score of above 2 points.

Table 1 summarizes the clinical characteristics of the crohn's disease patients that participated in the study. As can be seen, overall 15 crohn's disease patients were included in the study, of which 8 women, 7 men, which average age was 37.5 years and their average CDAI was 289. Overall 12 patients with Crohn's disease in remission, of which 8 women and 4 men having the average age of 45 years and which average CDAI was 60 were included in the study.

Table 2 summarizes the characteristics of the five groups that were analyzed.

TABLE 2

The clinical characteristics of the five groups of individuals analyzed.

| Study Group | Number of patients | % Female | Sema3A expression on CD4$^+$CD25$^+$ Mean (%) ± SEM | Mean CRP (mg/L) |
|---|---|---|---|---|
| Active Crohn's | 15 | 53.3% | 64.5% ± 14.49% | 99.3 |
| Silent Crhon's | 12 | 66.7% | 77.6 ± 9.93 | 5.3 |
| Active ulcerative colitis | 10 | 60% | 49.8 ± 16.45 | 46.8 |
| Acute diverticulitis | 10 | 50% | 73.9 ± 4.79 | 88.1 |
| Healthy Controls | 12 | 50% | 88.7 ± 3.6 | 4.6 |

Treg Cells Expressing Sema3A

The percentage (%) of Tregs (CD4+ CD25+high T cells) expressing sema3A in all studied groups (e.g., CD patients at remission and at relapse, UC patients at disease onset, patients suffering from acute diverticulitis and normal healthy controls) was performed on purified mononuclear cells, gating on CD4+CD25high cells and staining them with monoclonal antibodies: human anti-CD4 FITC/PE and CD25 PC5 (Immunotech, Beckman-Coulter, Marseille, France), and human anti-sema3A AlexaFluor 488 (R&D,

TABLE 1

The clinical and personal characteristics of the crohn's disease patients.

| Patient No. | Age (Years) | Gender | Sema3A expression on CD4$^+$CD25$^+$ (%) | CDAI | CRP (mg/L) | Treatment |
|---|---|---|---|---|---|---|
| | Active Crohn | | | | | |
| 1 | 40 | Female | 66.3% | 252 | 80.7 | P; ABX |
| 2 | 28 | Male | 65.9% | 222 | 14 | 5-ASA; P; 6-MP |
| 3 | 26 | Male | 74.5% | 358 | 222.3 | P; 6-MP; ABX |
| 4 | 46 | Female | 73.6% | 328 | 249.3 | 5-ASA; P; MTX; ABX |
| 5 | 55 | Female | 64.1% | 215 | 33.4 | 5-ASA; 6-MP |
| 6 | 21 | Female | 75% | 339 | 123.4 | 5-ASA; P; ABX |
| 7 | 23 | Female | 59% | 220 | 17 | 5-ASA; P |
| 8 | 22 | Male | 78.2% | 244 | 13.4 | 6-MP |
| 9 | 24 | Male | 69% | 389 | 208.6 | 5-ASA; P; 6-MP |
| 10 | 70 | Male | 68% | 302 | 73.8 | 5-ASA; P |
| 11 | 38 | Female | 74% | 292 | 102.3 | P; AZA |
| 12 | 36 | Male | 52.2% | 324 | 219.7 | P; 6-MP; ABX |
| 13 | 69 | Female | 63.8% | 289 | 61 | 5-ASA; B; ABX |
| 14 | 27 | Male | 57.1% | 301 | 81.6 | P |
| 15 | 40 | Female | 74% | 267 | 19 | P; 6-MP |
| | Silent Crohn | | | | | |
| 16 | 62 | Female | 86.7% | 66 | 1 | 5-ASA |
| 17 | 44 | Female | 84.6% | 41 | 3.6 | 5-ASA; P |
| 18 | 52 | Male | 90.4% | 32 | 5.8 | AZA |
| 19 | 30 | Male | 87% | 35 | 1.2 | 6-MP |
| 20 | 28 | Male | 79% | 80 | 16.9 | 5-ASA |
| 21 | 29 | Male | 82% | 110 | 14.7 | 5-ASA; 6-MP |
| 22 | 59 | Female | 78.2% | 56 | 4.5 | 5-ASA |
| 23 | 47 | Female | 77.1% | 44 | 2.9 | 5-ASA |
| 24 | 40 | Female | 59.1% | 59 | 0.7 | 5-ASA |
| 25 | 62 | Female | 64.2% | 41 | 3.4 | 5-ASA; P |
| 26 | 55 | Female | 65.1% | 69 | 8 | 5-ASA |
| 27 | 33 | Female | 77.7% | 38 | 0.8 | 5-ASA; P |

Abbreviations: 5-ASA, 5-aminosalicylic acid; 6-MP, 6-mercaptopurine; ABX, antibiotics (combination of metronidazole and ciprofloxacin); AZA, azathioprine; B, budesonide; P, prednisone; MTX, methotrexate; Sema3A, Semaphorin 3A.

Minneapolis, Minn., USA), and evaluated using flow cytometry software (FC500 and CXP software, Beckman Coulter, Brea, Calif., USA). The results are shown as % of Treg cells expressing sema3A, taking into consideration that the absolute number of Treg cells in all groups was found to be comparable. The threshold of Treg cells expressing sema3A was defined to be above 2.5 Mean-Fluorescent-Intensity (MFI) (Beckman-Coulter FACS, FC-500 Software). Standard deviation (STDEV) was used to quantify the amount of variation of a set of data values (e.g. percentage of Treg cells expressing sema 3A among the patients in each indicated group of disease or normal control).

Figure 1B:
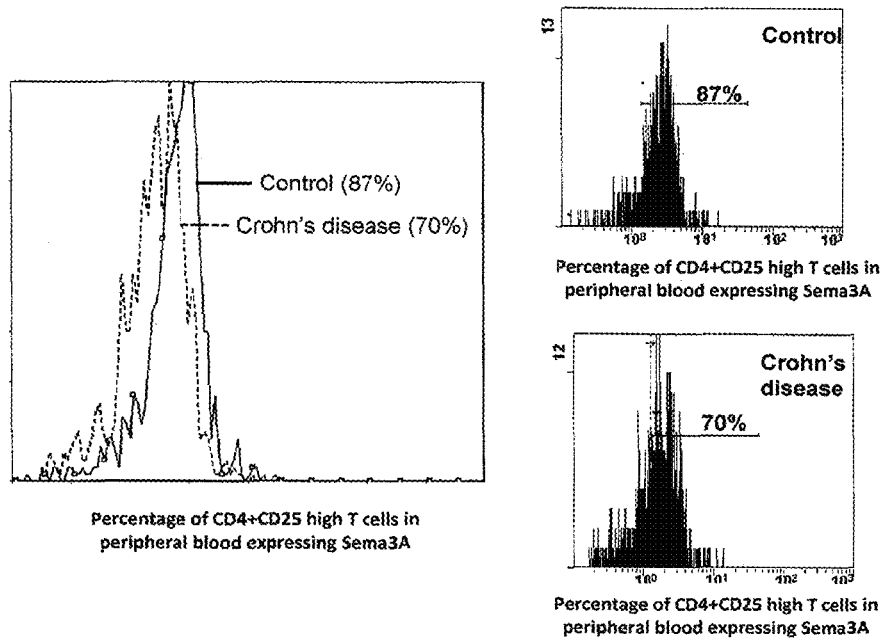
FIG. 1B is a representative FACS diagram showing analysis of Treg cells expressing sema3A in a CD patient compared to normal individual.
Figure 1C:
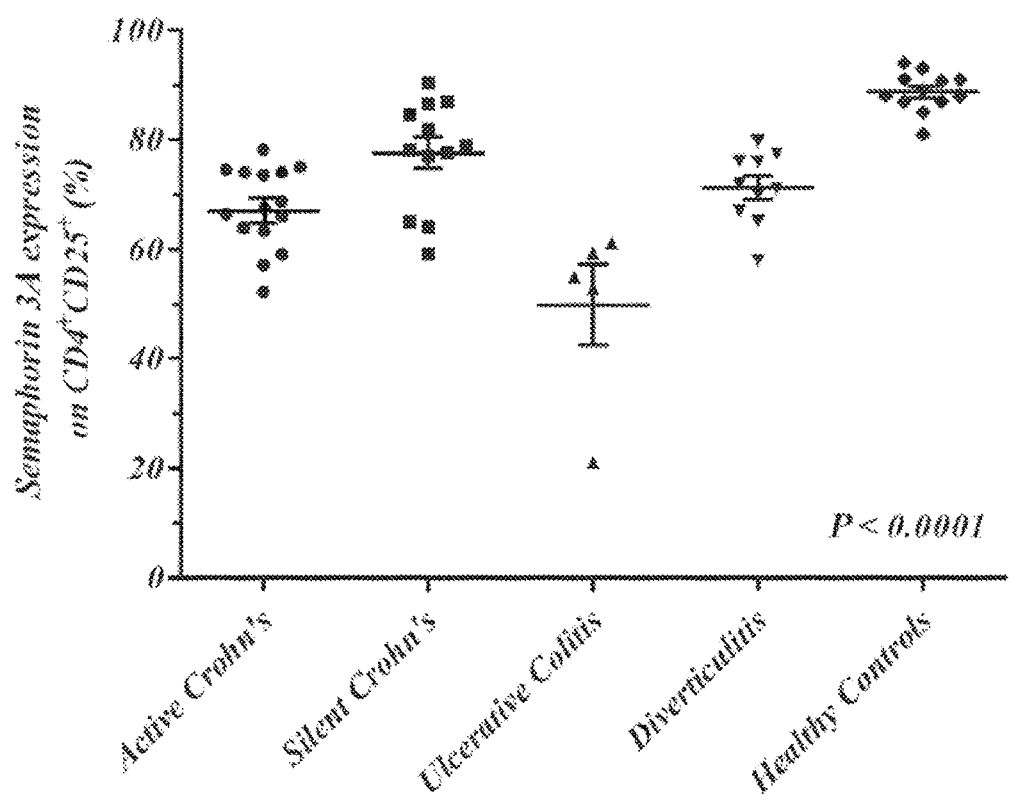
FIG. 1C is a dot plot demonstrating Semaphorin 3A expression on T regulatory cells (CD4+\CD25+) in various patients and in healthy subjects (control). Results are presented as percentages of T regulatory cells (CD4+\CD25+) expressing Semaphorin 3A on their membranes.

As can be seen in FIGS. 1A-1C, and table 2, the expression of Sema3A on CD4+CD25+ T cells was different among the five study groups.

The percentage of Treg cells (CD4+CD25high cells) in peripheral blood expressing sema3A was found to be significantly lower in patients with active CD (64.5%±14.49%) compared to 88.7%±3.6% in healthy individuals (p<0.001). This was also found to be significantly lower in CD patients in remission (77.6%±9.93%, p<0.001) and in patients with active UC and diverticulitis (49.8%±16.45%, p<0.0001 and 73.9%±4.79%, respectively).

No significant difference was found between the expression of Sema3A on CD4+CD25+ T cells of patients with silent Crohn's disease and healthy subjects or between patients with silent Crohn's disease and patients with acute diverticulitis.

Figure 2:
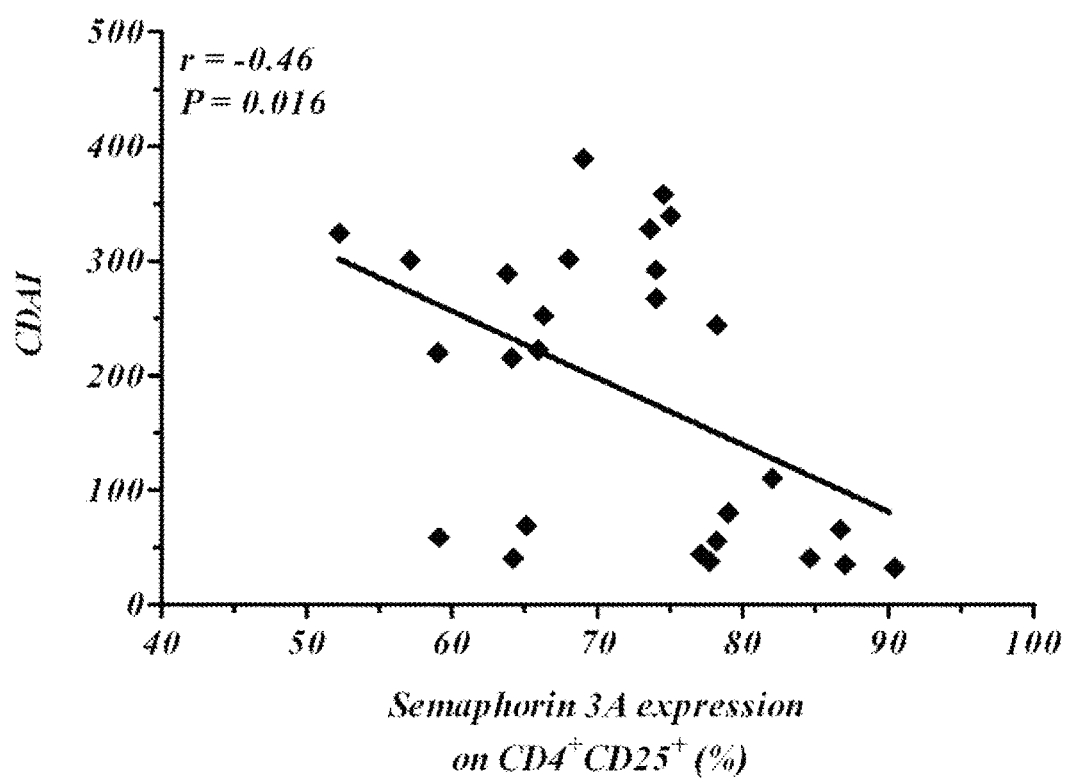
FIG. 2 is a dot plot demonstrating Semaphorin 3A expression on T regulatory cells (CD4+\CD25+) versus the CDAI in active and silent crohn's disease patients. The percentage of Treg cells expressing sema3A in peripheral blood of CD patients is found to be in negative correlation with the CDAI score (r=−0.46, p=0.016).

Example 2: An Inverse Correlation Between the Percentage of Treg Cells Expressing Sema3A and CDAI Score The clinical correlation between the percentage of Treg cells expressing sema3A taken from peripheral blood of CD patients and the CDAI scores of these patients was further analyzed. As can be seen in FIG. 2, the expression of Sema3A on CD4+CD25+ T cells of patients with Crohn's disease (silent and active) was found to be in inverse correlation with CDAI (Crohn's Disease Activity Index) (R=−0.46, P=0.016) (see FIG. 2 and Table 1), but no significant correlation was found with serum CRP levels (R=0.134, P=NS; data not shown). The expression of Sema3A on CD19+CD25+ B cells of patients with Crohn's disease was similar to that of healthy controls.

Example 3: Serum Levels of Sema3A

Serum samples were produced from all studied individuals during the study and were stored at −20° until analyzed together by ELISA. Commercial ELISA kits for both semaphorins (MBS-MyBiosource, San Diego, Calif., USA). Assessment was performed according to the manufacturer's instructions.

Serum levels of sema3A were found to be mildly lower in CD and UC patients but with no significant statistical difference when compared to that of healthy individuals (data not shown).

Example 4: Expression Pattern of Sema 3A in Patients Afflicted With a Bowel Disease A retrospective study which included colon biopsies form individuals at various stages of bowel diseases was conducted. Colonic biopsies were obtained from the following groups: (a) patients with active crohn's disease (n=20); patients with active ulcerative colitis (n=10), patients with acute diverticulitis (n=10); and healthy individuals (control, n=10). The expression of Sema3A in intestine was assessed and compared between the four aforementioned groups. Immunohistochemistry staining of Sema3A was conducted on 5 μm slices of biopsies. The staining intensities were graded according to scores of 0-3, wherein a score of 0 was defined when no staining was observed, score 3 was defined when a maximal staining was observed. An average grading was calculated for each biopsy and group of patients and statistical analysis was conducted.

Figure 3:
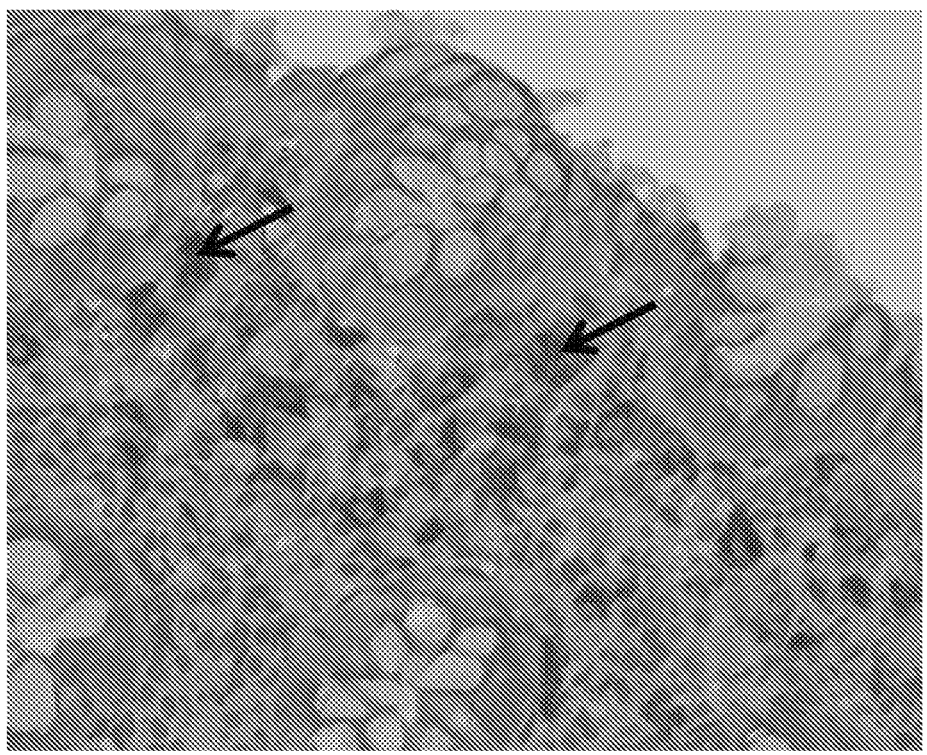
FIG. 3 is a micrograph of a representative colon tissue section of a patient afflicted with crohn's disease in the active state, showing Sema 3A staining using a specific antibody. Arrows indicate positive Sema 3A immunostaining of macrophages in the lamina propria.

A similar sema3A expression pattern was seen in the four groups tested. In the majority of specimens macrophages as well as lymphocytes in staining intensities of 3 and 2, respectively was demonstrated in the lamina propria (FIG. 3). In addition, a positive neuroendocrine staining was observed in the crypts.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is to be understood that further trials are being conducted to establish clinical effects.

---

The invention claimed is:

1. A method for alleviating symptoms of inflammatory bowel disease (IBD) in a subject in need thereof, said method comprising administering to the subject a pharmaceutical composition comprising a therapeutically effective amount of Semaphorin 3A, said Semaphorin 3A consisting of SEQ ID NO: 1, thereby alleviating symptoms of IBD in the subject.

2. The method of claim 1, wherein said IBD is selected from the group consisting of: Crohn's disease, and ulcerative colitis.

3. The method of claim 2, wherein said IBD is Crohn's disease.

4. The method of claim 2, wherein said IBD is ulcerative colitis.

5. The method of claim 1, wherein said administering is via a route selected from the group consisting of: oral, rectal and intravenous.

6. The method of claim 3, wherein said alleviating symptoms results in a decrease in the Crohn's Disease Activity Index (CDAI) value of said subject.

* * * * *

SEQUENCE LISTING

```
<160> NUMBER OF SEQ ID NOS: 2

<210> SEQ ID NO 1
<211> LENGTH: 771
<212> TYPE: PRT
<213> ORGANISM: Homo sapiens

<400> SEQUENCE: 1

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
```

```
                     35                  40                  45
Asn Gly Leu Ala Asn Ser Ser Tyr His Thr Phe Leu Leu Asp Glu
                 50                  55                  60
Glu Arg Ser Arg Leu Tyr Val Gly Ala Lys Asp His Ile Phe Ser Phe
65                  70                  75                  80
Asp Leu Val Asn Ile Lys Asp Phe Gln Lys Ile Val Trp Pro Val Ser
                 85                  90                  95
Tyr Thr Arg Arg Asp Glu Cys Lys Trp Ala Gly Lys Asp Ile Leu Lys
                100                 105                 110
Glu Cys Ala Asn Phe Ile Lys Val Leu Lys Ala Tyr Asn Gln Thr His
                115                 120                 125
Leu Tyr Ala Cys Gly Thr Gly Ala Phe His Pro Ile Cys Thr Tyr Ile
                130                 135                 140
Glu Ile Gly His His Pro Glu Asp Asn Ile Phe Lys Leu Glu Asn Ser
145                 150                 155                 160
His Phe Glu Asn Gly Arg Gly Lys Ser Pro Tyr Asp Pro Lys Leu Leu
                165                 170                 175
Thr Ala Ser Leu Leu Ile Asp Gly Glu Leu Tyr Ser Gly Thr Ala Ala
                180                 185                 190
Asp Phe Met Gly Arg Asp Phe Ala Ile Phe Arg Thr Leu Gly His His
                195                 200                 205
His Pro Ile Arg Thr Glu Gln His Asp Ser Arg Trp Leu Asn Asp Pro
210                 215                 220
Lys Phe Ile Ser Ala His Leu Ile Ser Glu Ser Asp Asn Pro Glu Asp
225                 230                 235                 240
Asp Lys Val Tyr Phe Phe Arg Glu Asn Ala Ile Asp Gly Glu His
                245                 250                 255
Ser Gly Lys Ala Thr His Ala Arg Ile Gly Gln Ile Cys Lys Asn Asp
                260                 265                 270
Phe Gly Gly His Arg Ser Leu Val Asn Lys Trp Thr Thr Phe Leu Lys
                275                 280                 285
Ala Arg Leu Ile Cys Ser Val Pro Gly Pro Asn Gly Ile Asp Thr His
                290                 295                 300
Phe Asp Glu Leu Gln Asp Val Phe Leu Met Asn Phe Lys Asp Pro Lys
305                 310                 315                 320
Asn Pro Val Val Tyr Gly Val Phe Thr Thr Ser Ser Asn Ile Phe Lys
                325                 330                 335
Gly Ser Ala Val Cys Met Tyr Ser Met Ser Asp Val Arg Arg Val Phe
                340                 345                 350
Leu Gly Pro Tyr Ala His Arg Asp Gly Pro Asn Tyr Gln Trp Val Pro
                355                 360                 365
Tyr Gln Gly Arg Val Pro Tyr Pro Arg Pro Gly Thr Cys Pro Ser Lys
                370                 375                 380
Thr Phe Gly Gly Phe Asp Ser Thr Lys Asp Leu Pro Asp Asp Val Ile
385                 390                 395                 400
Thr Phe Ala Arg Ser His Pro Ala Met Tyr Asn Pro Val Phe Pro Met
                405                 410                 415
Asn Asn Arg Pro Ile Val Ile Lys Thr Asp Val Asn Tyr Gln Phe Thr
                420                 425                 430
Gln Ile Val Val Asp Arg Val Asp Ala Glu Asp Gly Gln Tyr Asp Val
                435                 440                 445
Met Phe Ile Gly Thr Asp Val Gly Thr Val Leu Lys Val Val Ser Ile
                450                 455                 460
```

```
Pro Lys Glu Thr Trp Tyr Asp Leu Glu Glu Val Leu Leu Glu Glu Met
465                 470                 475                 480
Thr Val Phe Arg Glu Pro Thr Ala Ile Ser Ala Met Glu Leu Ser Thr
                485                 490                 495
Lys Gln Gln Gln Leu Tyr Ile Gly Ser Thr Ala Gly Val Ala Gln Leu
            500                 505                 510
Pro Leu His Arg Cys Asp Ile Tyr Gly Lys Ala Cys Ala Glu Cys Cys
            515                 520                 525
Leu Ala Arg Asp Pro Tyr Cys Ala Trp Asp Gly Ser Ala Cys Ser Arg
        530                 535                 540
Tyr Phe Pro Thr Ala Lys Arg Arg Thr Arg Gln Asp Ile Arg Asn
545                 550                 555                 560
Gly Asp Pro Leu Thr His Cys Ser Asp Leu His His Asp Asn His His
                565                 570                 575
Gly His Ser Pro Glu Glu Arg Ile Ile Tyr Gly Val Glu Asn Ser Ser
            580                 585                 590
Thr Phe Leu Glu Cys Ser Pro Lys Ser Gln Arg Ala Leu Val Tyr Trp
            595                 600                 605
Gln Phe Gln Arg Arg Asn Glu Glu Arg Lys Glu Ile Arg Val Asp
        610                 615                 620
Asp His Ile Ile Arg Thr Asp Gln Gly Leu Leu Leu Arg Ser Leu Gln
625                 630                 635                 640
Gln Lys Asp Ser Gly Asn Tyr Leu Cys His Ala Val Glu His Gly Phe
                645                 650                 655
Ile Gln Thr Leu Leu Lys Val Thr Leu Glu Val Ile Asp Thr Glu His
            660                 665                 670
Leu Glu Glu Leu Leu His Lys Asp Asp Asp Gly Asp Gly Ser Lys Thr
        675                 680                 685
Lys Glu Met Ser Asn Ser Met Thr Pro Ser Gln Lys Val Trp Tyr Arg
        690                 695                 700
Asp Phe Met Gln Leu Ile Asn His Pro Asn Leu Asn Thr Met Asp Glu
705                 710                 715                 720
Phe Cys Glu Gln Val Trp Lys Arg Asp Arg Lys Gln Arg Gln Arg Gln
                725                 730                 735
Pro Gly His Thr Pro Gly Asn Ser Asn Lys Trp Lys His Leu Gln Glu
            740                 745                 750
Asn Lys Lys Gly Arg Asn Arg Arg Thr His Glu Phe Glu Arg Ala Pro
        755                 760                 765
Arg Ser Val
    770
```

<210> SEQ ID NO 2
<211> LENGTH: 2316
<212> TYPE: DNA
<213> ORGANISM: Artificial Sequence
<220> FEATURE:
<223> OTHER INFORMATION: cDNA

<400> SEQUENCE: 2

```
atgggctggt taactaggat tgtctgtctt ttctggggag tattacttac agcaagagca      60
aactatcaga tgggaagaa caatgtgcca aggctgaaat tatcctacaa agaaatgttg     120
gaatccaaca atgtgatcac ttcaatggc ttggccaaca gctccagtta tcataccttc     180
cttttggatg aggaacggag taggctgtat gttggagcaa aggatcacat attttcattc    240
```

```
gacctggtta atatcaagga ttttcaaaag attgtgtggc cagtatctta caccagaaga    300
gatgaatgca agtgggctgg aaaagacatc ctgaaagaat gtgctaattt catcaaggta    360
cttaaggcat ataatcagac tcacttgtac gcctgtggaa cgggggcttt tcatccaatt    420
tgcacctaca ttgaaattgg acatcatcct gaggacaata ttttttaagct ggagaactca    480 cattttgaaa acggccgtgg gaagagtcca tatgaccctra agctgctgac agcatccctt    540
ttaatagatg gagaattata ctctggaact gcagctgatt ttatggggcg agactttgct    600
atcttccgaa ctcttgggca ccaccaccca atcaggacag agcagcatga ttccaggtgg    660
ctcaatgatc caaagttcat tagtgcccac ctcatctcag agagtgacaa tcctgaagat    720
gacaaagtat acttttttctt ccgtgaaaat gcaatagatg gagaacactc tggaaaagct    780
actcacgcta gaataggtca gatatgcaag aatgactttg gagggcacag aagtctggtg    840
aataaatgga caacattcct caaagctcgt ctgatttgct cagtgccagg tccaaatggc    900
attgacactc attttgatga actgcaggat gtattcctaa tgaactttaa agatcctaaa    960
aatccagttg tatatggagt gtttacgact tccagtaaca ttttcaaggg atcagccgtg   1020
tgtatgtata gcatgagtga tgtgagaagg gtgttccttg gtccatatgc ccacagggat   1080
ggacccaact atcaatgggt gccttatcaa ggaagagtcc cctatccacg gccaggaact   1140
tgtcccagca aaacatttgg tggttttgac tctacaaagg accttcctga tgatgttata   1200
acctttgcaa gaagtcatcc agccatgtac aatccagtgt ttcctatgaa caatcgccca   1260
atagtgatca aaacggatgt aaattatcaa tttacacaaa ttgtcgtaga ccgagtggat   1320
gcagaagatg gacagtatga tgttatgttt atcggaacag atgttgggac cgttcttaaa   1380
gtagtttcaa ttcctaagga gacttggtat gatttagaag aggttctgct ggaagaaatg   1440 acagttttttc gggaaccgac tgctatttca gcaatggagc tttccactaa gcagcaacaa   1500
ctatatattg gttcaacggc tggggttgcc cagctcccctt tacaccggtg tgatatttac   1560
gggaaagcgt gtgctgagtg ttgcctcgcc cgagacccctt actgtgcttg ggatggttct   1620
gcatgttctc gctatttttcc cactgcaaag agacgcacaa gacgacaaga tataagaaat   1680
ggagacccac tgactcactg ttcagactta caccatgata atcaccatgg ccacagccct   1740
gaagagagaa tcatctatgg tgtagagaat agtagcacat ttttggaatg cagtccgaag   1800
tcgcagagag cgctggtcta ttggcaattc cagaggcgaa atgaagagcg aaaagaagag   1860
atcagagtgg atgatcatat catcaggaca gatcaaggcc ttctgctacg tagtctacaa   1920
cagaaggatt caggcaatta cctctgccat gcggtggaac atgggttcat acaaactctt   1980
cttaaggtaa ccctggaagt cattgacaca gagcatttgg aagaacttct tcataaagat   2040
gatgatggag atggctctaa gaccaaagaa atgtccaata gcatgacacc tagccagaag   2100
gtctggtaca gagacttcat gcagctcatc aaccaccccca atctcaacac aatggatgag   2160
ttctgtgaac aagtttggaa aagggaccga aaacaacgtc ggcaaaggcc aggacatacc   2220
ccagggaaca gtaacaaatg gaagcactta caagaaaata agaaaggtag aaacaggagg   2280
acccacgaat ttgagagggc acccaggagt gtctga                            2316
```